US011309072B2

(12) United States Patent
Carmi

(10) Patent No.: US 11,309,072 B2
(45) Date of Patent: Apr. 19, 2022

(54) SYSTEMS AND METHODS FOR FUNCTIONAL IMAGING

(71) Applicant: GE Precision Healthcare LLC, Wauwatosa, WI (US)

(72) Inventor: Raz Carmi, Haifa (IL)

(73) Assignee: GE PRECISION HEALTHCARE LLC, Wauwatosa, WI (US)

(*) Notice: Subject to any disclaimer, the term of this patent is extended or adjusted under 35 U.S.C. 154(b) by 121 days.

(21) Appl. No.: 16/854,603

(22) Filed: Apr. 21, 2020

(65) Prior Publication Data

US 2021/0327560 A1 Oct. 21, 2021

(51) Int. Cl.
*G16H 30/20* (2018.01)
*G06T 7/00* (2017.01)
*G06T 11/00* (2006.01)

(52) U.S. Cl.
CPC ........... *G16H 30/20* (2018.01); *G06T 7/0012* (2013.01); *G06T 11/006* (2013.01); *G06T 2207/20076* (2013.01); *G06T 2207/30024* (2013.01)

(58) Field of Classification Search
CPC ..... G16H 30/20; G06T 7/0012; G06T 11/006; G06T 2207/20076; G06T 2207/30024
See application file for complete search history.

(56) References Cited

U.S. PATENT DOCUMENTS 6,728,424 B1 4/2004 Zhu
6,740,883 B1 5/2004 Stodilka
(Continued)

FOREIGN PATENT DOCUMENTS

WO 2009138898 A1 11/2009

OTHER PUBLICATIONS

Saad et al., "A new method for improving functional-to-structural MRI alignment using local Pearson correlation", NeuroImage, vol. 44, Issue 3, 2009, pp. 839-848. (Year: 2009).*

(Continued)

*Primary Examiner* — Vu Le
*Assistant Examiner* — Julius Chai
(74) *Attorney, Agent, or Firm* — The Small Patent Law Group LLC; Dean D. Small

(57) ABSTRACT

A system includes a structural imaging acquisition unit, a functional imaging acquisition unit, and one or more processors. The structural imaging acquisition unit is configured to perform a structural scan to acquire structural imaging information of a patient. The functional imaging acquisition unit is configured to perform a functional scan to acquire functional imaging information of a patient. The one or more processors are configured to generate a tissue-specific anatomical probability map using the structural imaging information; generate a tissue-non-specific anatomical probability map using the structural imaging information; generate local combined anatomical probability weights using the tissue-specific anatomical probability map, the tissue-non-specific anatomical probability map, and the functional image data; re-distribute the functional image data using the local combined anatomical probability weights to provide re-distributed functional volumetric data; and generate an image using the re-distributed functional volumetric data.

20 Claims, 16 Drawing Sheets

(56) References Cited

U.S. PATENT DOCUMENTS

| | | | |
|---|---|---|---|
| 6,878,941 B2 | 4/2005 | Balan | |
| 7,324,842 B2 | 1/2008 | Dale | |
| 7,348,564 B2 | 3/2008 | Wollenweber | |
| 7,822,241 B2 | 10/2010 | Eck | |
| 8,423,118 B2 | 4/2013 | Wenzel | |
| 8,447,090 B2 | 5/2013 | Wakai | |
| 8,989,464 B2 | 3/2015 | Carmi | |
| 9,532,762 B2 | 1/2017 | Cho | |
| 9,730,663 B2 | 8/2017 | Koehler | |
| 9,818,191 B2 | 11/2017 | Magda | |
| 9,905,044 B1 | 2/2018 | Carmi | |
| 9,922,433 B2 * | 3/2018 | Schieke | G06K 9/6281 |
| 2003/0004405 A1 | 1/2003 | Townsend | |
| 2003/0216631 A1 | 11/2003 | Block | |
| 2004/0071325 A1 | 4/2004 | Joseph Declerck | |
| 2005/0226527 A1 | 10/2005 | Weese | |
| 2007/0258908 A1 | 11/2007 | Lanza | |
| 2008/0009698 A1 | 1/2008 | Boese | |
| 2008/0064949 A1 | 3/2008 | Hertel | |
| 2008/0095414 A1 | 4/2008 | Desh | |
| 2008/0123922 A1 | 5/2008 | Gielen | |
| 2009/0202125 A1 | 8/2009 | Zhao | |
| 2012/0099770 A1 | 4/2012 | Cagnan | |
| 2013/0004038 A1 * | 1/2013 | Carmi | G06T 5/002 382/128 |
| 2015/0003709 A1 * | 1/2015 | Boernert | A61B 6/032 382/131 |
| 2016/0300343 A1 | 10/2016 | Gazit | |
| 2016/0343127 A1 * | 11/2016 | Miller | A61B 5/055 |
| 2017/0287175 A1 * | 10/2017 | Lin | G06K 9/6281 |
| 2017/0323177 A1 | 11/2017 | Sauer | |
| 2018/0061113 A1 * | 3/2018 | Carmi | G06T 7/0012 |
| 2018/0211419 A1 * | 7/2018 | Zhu | G06T 7/11 |
| 2019/0209116 A1 * | 7/2019 | Sjostrand | A61B 6/467 |
| 2021/0264645 A1 * | 8/2021 | Polak | G06K 9/6215 |
| 2021/0267474 A1 * | 9/2021 | Wang | G06N 3/08 |

OTHER PUBLICATIONS

Adrien Le Pogam, Conditional Partial Volume Correction for Emission Tomography: A Wavelet-Based Hidden Markov Model and Multi-Resolution Approach, IEEE-2008; International Symposium on Biomedical Imaging, 1. U619 INSERM, CHRU Bretonneau, Tours, France, 2. U650 INSERM, LaTIM, CHU Morvan, Brest, France, 3. Imperial College, London, England, May 2008.

Alvarez, L., et al.; Image Selective Smoothing and Edge Detection by Nonlinear Diffusion; 1992; SIAM Journal of Numerical Analysis; 29(3)845-866.

Boussion, N., et al.; Incorporation of wavelet-based denoising in iterative deconvolution for partial volun;ie correction in whole-body PET imaging; 2009; European Journal of Nuclear Medicine and Molecular Imaging; 36(7).

Boussion, N., et al.; Fully Automated Partial Volume Correction in PET Based on a Wavelet Approach without the use of Anatomical Information; 2007; IEEE Trans. on Nuclear Science Symposium and Medical Imaging; Paper M12-5.

Catte, F., et al.; Image Selective Smoothing and Edge Detection by Nonlinear Diffusion; 1992; SIAM Journal on Numerical Analysis; 29(1 )182-193.

Douiri, A., et al.; Anisotropic diffusion regularization methods for diffuse optical tomography using edge prior information; 2007; Measurement Science and Technology; 18:87-95.

Gerig, G., et al.; Nonlinear Anisotropic Filtering of MRI Data; 1992; IEEE Trans, on Medical Imaging; 11(2); 221-232.

Kirov, A. S., et al.; Partial volume effect correction in PET using regularized iterative deconvolution with variance control based on local topology; 2008; Phys. Med. Biol.; 53:2577-2591.

Le Pogam, A., et al.; Conditional Partial Volume Correction for Emission Tomography: A Wavelet-based Hidden Markov Model and Multi-Resolution Approach; 2008; IEEE Trans. on Int'l Symposium on Biomedical Imaging; pp. 1319-1322.

Perona, P., et al.; Scale-Space and Edge Detection Using Anisotropic Diffusion; 1990; IEEE Trans. on Pattern Analysis and Machine Intelligence; 12(7)629-639.

Soret, M., et al.; Partial-Volume Effect in PET Tumor Imaging; 2007; The Journal of Nuclear Medicine; 48(6)932-945.

Turkheimer, F. E., et al.; PET Image Denoising Using a Synergistic Multiresolution Analysis of Structural (MRI/CT) and Functional Datasets; 2008; Journal of Nuclear Medicine; pp. 657-666.

Wiemker, R., et al.; Combined motion blur and partial volume correction for computer aided diagnosis of pulmonary nodules in PET/CT; 2008; Int. J_ CARS; 3:105-113.

* cited by examiner

Redistribution weights from P1 (as source) to P2 (as target) and from P2 (as source) to P1 (as target):

Weights with specific model only: Ws_2to1 = 1.0 , Ws_1to2 = 0.5 -> normalize -> Ws_2to1 = 0.333, Ws_1to2 = 0.666

Weights with non-specific model only: Wn_2to1 = 1.0, Wn_1to2 = 0.1 -> normalize -> Wn_2to1 = 0.91, Wn_1to2 = 0.09

Combined two model weights: = Ws* Wn: Wc_2to1 = 0.3 , Wc_1to2 = 0.06 -> normalize -> Wc_2to1 = 0.83 , Wc_1to2 = 0.17

Combined two model weights with regularization bias: = Ws* (Wn + 2):
Wc_2to1 = 0.333*(0.91+2) , Wc_1to2 = 0.666* (0.09+2) -> normalize -> Wc_2to1 = 0.41, Wc_1to2 = 0.59

FIG. 3H

Two voxels along a profile for which redistribution weights can be calculated

Redistribution weights from P1 (as source) to P2 (as target) and from P2 (as source) to P1 (as target):

Weights with specific model only: $Ws\_2to1 = 1.0$, $Ws\_1to2 = 0.5$ -> normalize -> $Ws\_2to1 = 0.333$, $Ws\_1to2 = 0.666$ Weights with non-specific model only: $Wn\_2to1 = 1.0$, $Wn\_1to2 = 0.1$ -> normalize -> $Wn\_2to1 = 0.09$, $Wn\_1to2 = 0.91$ Combined two model weights: $= Ws * Wn$: $Wc\_2to1 = 0.03$, $Wc\_1to2 = 0.6$ -> normalize -> $Wc\_2to1 = 0.05$, $Wc\_1to2 = 0.95$ Combined two model weights with regularization bias: $= Ws * (Wn + 2)$:
$Wc\_2to1 = 0.333*(0.09+2)$, $Wc\_1to2 = 0.666*(0.91+2)$ -> normalize -> $Wc\_2to1 = 0.26$, $Wc\_1to2 = 0.74$

FIG. 4H

SYSTEMS AND METHODS FOR FUNCTIONAL IMAGING

BACKGROUND OF THE INVENTION

The subject matter disclosed herein relates generally to systems and methods for imaging (e.g., diagnostic imaging of a patient).

Multi-modality imaging may be used to acquire both functional and structural imaging information. In conventional multi-modality systems, however, structural accuracy of the functional information may be insufficient. For example, the accuracy or resolution of the functional information may not be sufficient for reliable clinical usage.

BRIEF DESCRIPTION OF THE INVENTION

In one embodiment, a system is provided that includes a structural imaging acquisition unit, a functional imaging acquisition unit, and one or more processors. The structural imaging acquisition unit is configured to perform a structural scan to acquire structural imaging information of a patient. The functional imaging acquisition unit is configured to perform a functional scan to acquire functional imaging information of a patient. The one or more processors are configured to generate a tissue-specific anatomical probability map using the structural imaging information; generate a tissue-non-specific anatomical probability map using the structural imaging information; generate local combined anatomical probability weights using the tissue-specific anatomical probability map, the tissue-non-specific anatomical probability map, and the functional image data; re-distribute the functional image data using the local combined anatomical probability weights to provide re-distributed functional volumetric data; and generate an image using the re-distributed functional volumetric data.

In another embodiment, a method is provided. The method includes obtaining structural imaging information of a patient including anatomical volumetric data, and obtaining functional imaging information of the patient including functional volumetric data. Also, the method includes generating a tissue-specific anatomical probability map using the structural imaging information, and generating a tissue-non-specific anatomical probability map using the structural imaging information. Further, the method includes generating local combined anatomical probability weights using the tissue-specific anatomical probability map, the tissue-non-specific anatomical probability map, and the functional image data. The method also includes re-distributing the functional image data using the local combined anatomical probability weights to provide re-distributed functional volumetric data, and generating an image using the re-distributed functional volumetric data.

In another embodiment, a tangible and non-transitory computer readable medium is provided. The tangible and non-transitory computer readable medium includes one or more computer software modules configured to direct one or more processors. The tangible and non-transitory computer readable medium is configured to direct the one or more processors to: obtain structural imaging information of a patient including anatomical volumetric data; obtain a functional imaging information of the patient including functional volumetric data; generate a tissue-specific anatomical probability map using the structural imaging information; generate a tissue-non-specific anatomical probability map using the structural imaging information; generate local combined anatomical probability weights using the tissue-specific anatomical probability map, the tissue-non-specific anatomical probability map, and the functional image data; re-distribute the functional image data using the local combined anatomical probability weights to provide re-distributed functional volumetric data; and generate an image using the re-distributed functional volumetric data.

BRIEF DESCRIPTION OF THE DRAWINGS

FIG. 3h depicts calculation of weights for the data of FIGS. 3a and 3b.

FIG. 4h depicts calculation of weights for the data of FIGS. 4a and 4b.

DETAILED DESCRIPTION OF THE INVENTION

Figure 1:
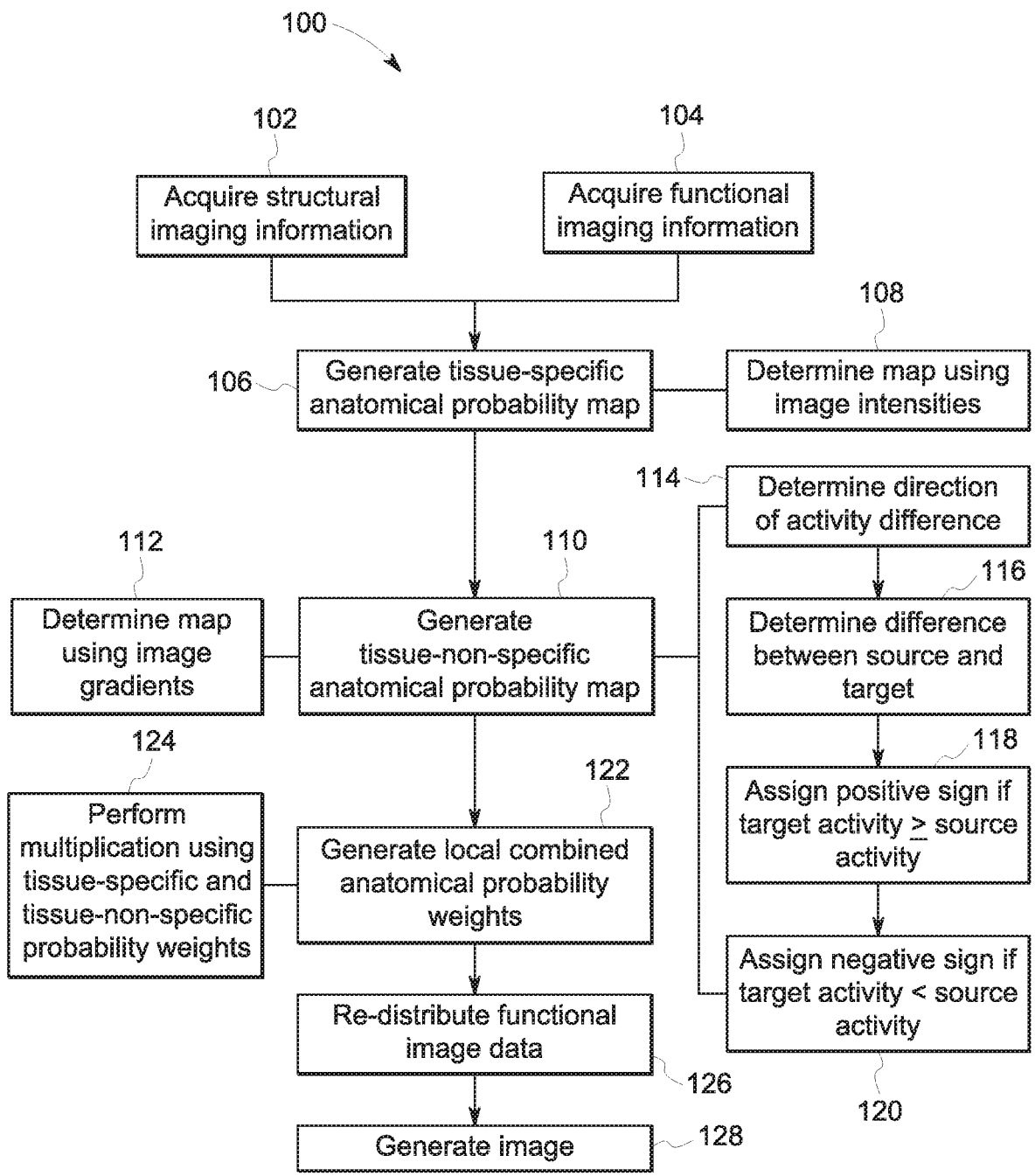
FIG. 1 is a flowchart of a method in accordance with various embodiments described herein.
Figure 2A:
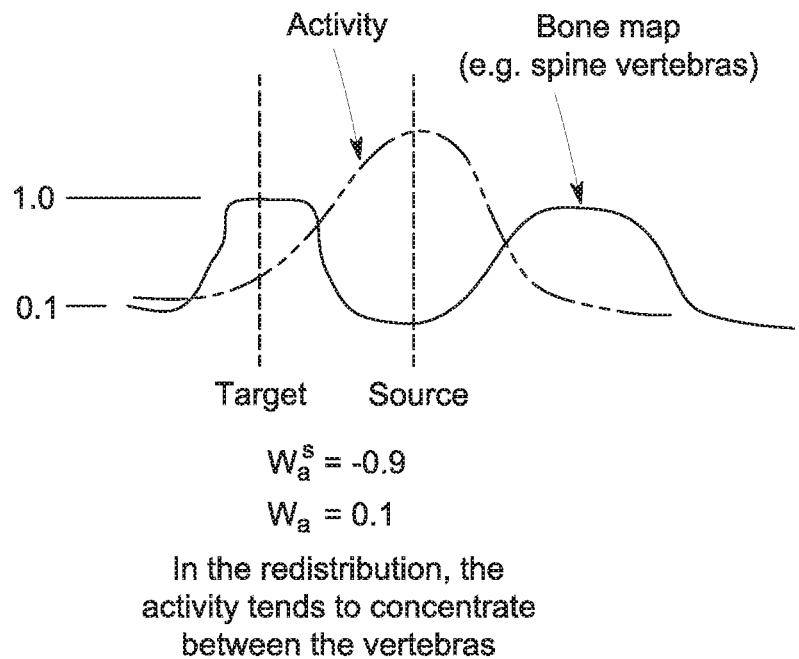
FIG. 2a provides a graph comparing activity with a bone map for a re-distribution in accordance with various embodiments.
Figure 2B:
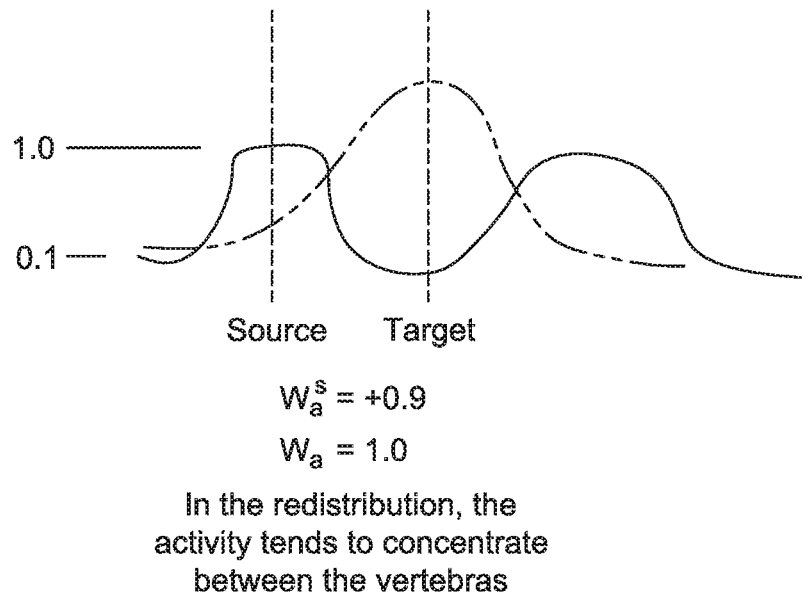
FIG. 2b provides a graph comparing activity with a bone map for a re-distribution in accordance with various embodiments FIG. 2c provides a graph comparing activity with a bone map for a re-distribution in accordance with various embodiments.
Figure 2C:
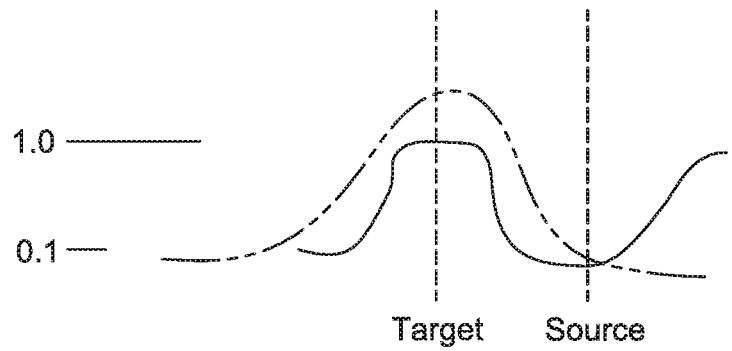
FIG. 2d provides a graph comparing activity with a bone map for a re-distribution in accordance with various embodiments.
Figure 2D:
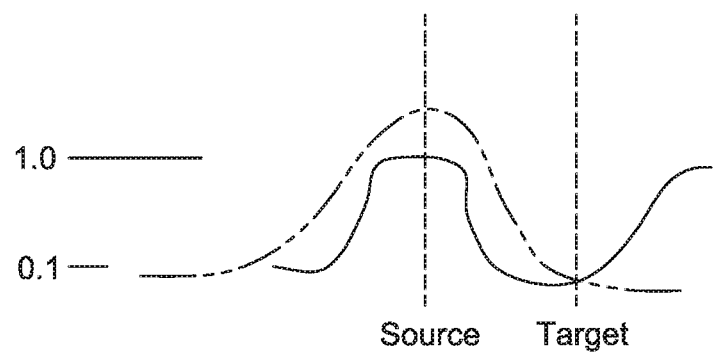

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for improving functional imaging data such as SPECT or PET in multi-modality imaging systems, based on corresponding anatomical imaging data such as CT or MM. Various embodiments utilize combined probability weights from both tissue-specific and tissue-non-specific models to re-distribute functional data.

A technical effect of various embodiments described herein includes improved diagnostic imaging. A technical effect of various embodiments includes improved resolution of functional imaging information. A technical effect of various embodiments includes improved correlation between functional and anatomical images.

FIG. 1 illustrates a flowchart of a method 100 (e.g., a method for medical imaging). The operations of FIG. 1 may be implemented by one or more processors executing program instructions stored in memory. The method 100, for example, may employ structures or aspects of various embodiments (e.g., systems and/or methods) discussed herein, such as the system 500 (see FIG. 5 and related discussion). In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 100 may be used as one or more algorithms to direct hardware to perform one or more operations described herein. It should be noted, other methods may be used, in accordance with embodiments herein.

Before addressing the individual depicted steps of the example method 100, a general overview is provided. First, functional and anatomical volumetric image data are obtained. For example, the functional and anatomical (anatomical may also be referred to as structural herein) volumetric image data may be obtained after tomographic reconstructions of acquired signals for the specific functional and anatomical modality systems. Generally, anatomical or structural imaging modality systems as used herein may be used to image structures (e.g., bone, brain, tissue) of an object (e.g., human patient) being scanned, while functional imaging modalities may be used to image function (e.g., uptake of a radiotracer or other agent) of the object. Examples of functional imaging modality systems include positron emission tomography (PET), single photon emission computed tomography (SPECT), or nuclear medicine (NM) imaging, as well as magneto-encephalography (MEG) or electric-encephalography (EEG), for example. Examples of structural imaging modality systems include x-ray, computed tomography (CT), magnetic resonance imaging (MM), and ultrasound (US). The functional volumetric image data may be referred to as a functional image volume or include a functional image volume, and the anatomical volumetric image data may be referred to as an anatomical image volume or include an anatomical image volume. The functional and anatomical image volumes in various embodiments are co-registered and/or resampled to obtain a convenient shared voxel grid for mutual processing. It may be noted that co-registration may be satisfied up to reasonable deviation errors (e.g., no more than several millimeters). For example, the functional image volume may be re-sampled to match the voxel grid of the anatomical image volume. It may be noted that in various embodiments, the same acquisition system may be used to provide both the functional and structural imaging information used as discussed herein. For example, unique targeted CT or MRI contrast materials may be utilized, and the CT or MM images may also provide functional information in addition to structural information. In some embodiments, other types of functional imaging information may be obtained by using techniques such as dynamic-CT, dynamic-MM, spectral-CT, or functional-MM, for example.

In some embodiments, before starting the image reformation processing (e.g., the process of adjusting one or more portions of the functional image volume to match one or more portions of the anatomical image volume), a set of analyzed voxels in the functional image volume and a corresponding set of neighbor voxels for each analyzed voxel are determined and, with respect to the neighbor voxels, a spatial weight distribution, or proximity weights, may be determined. The weights may be used to assign stronger correspondence where a neighbor voxel is closer to the analyzed voxel. For example, the weights may be determined as a 3D Gaussian function centered on the analyzed voxel.

Further, in some embodiments the anatomical data may be used as part of two processes. In the first process, preferred anatomical objects may be defined, for example based on the targeted clinical application and an a priori knowledge about the targeting properties of the tracer or agent used for the corresponding functional imaging. For example, in an example scenario of imaging related to diseases related to bones, the skeleton and bones may be segmented (sharply or softly) based on known image value ranges and/or structural models and priors. As another example, specific brain tissue, or tumor tissue, or a whole organ may be segmented. Further, in some embodiments, several different tissue types or organs may be segmented, such as the hard (cortical) bones and soft (trabecular) bones of the skeleton. Further still, in some embodiments, smoothed transition values or weights between different object types may be generated. Such smoothing may be beneficial, for example, where anatomical data itself may suffer from inaccuracies such as image noise or artifacts.

In the second process using the anatomical data, probability maps are defined based on the previous determination of anatomical objects, as discussed in more detail herein. The probability maps in various embodiments are based on a predefined model regarding the probability that the determined anatomical objects may express functional data signals (e.g., the probability that an anatomical object is represented in the functional image volume). It may further be noted that, in some embodiments, the probability map values may be spatially smoothed between different segments.

With the anatomical probability maps prepared, and the set of voxels in the functional image volume determined, one or more portions of the functional image may be re-distributed to improve image quality. Generally, all voxels to be analyzed may be processed, and functional image values are re-distributed across neighbor voxels to obtain reformed functional volumetric image data. The reformed or re-distributed functional data reflects calculated expectation levels that the functional information is essentially originated from the determined anatomical objects. The expectation levels may be determined locally based on several conditions and mathematical functions which include one or more aspects discussed herein. Accordingly, functional information having a higher correspondence (or likelihood of correspondence) with a particular structure may be re-distributed to better match, align with, or correspond to the location of the structure, and functional information having a lower correspondence (or likelihood of correspondence) with the particular structure may be unmodified from a previous location. Overall, it is likely that the quantitative accuracy of the functional information will be also improved in the re-distribution process. Additionally, the resulting re-distributed functional data may be re-sampled, for example to fit desired visual optimization or further processing. The final data is visualized (e.g., presented on a screen or print-out for a user). Optionally, the re-distributed final data may be presented visually with the original functional data and/or anatomical data. User confidence analysis of the image reformation results may also be provided. With a general overview having been provided, particular steps of the illustrated example are now discussed. It may be noted that one or more aspects discussed above (and/or variations thereof) may be utilized in one or more steps of the example method discussed below.

Generally, in various embodiments, the method 100 is used to construct both a tissue-specific anatomical probability map, and a tissue-non-specific anatomical probability map. Then, a balanced combined map (or weights) is generated that is used in a functional data re-distribution process that provides image enhancement. It may be noted that more than one probability map of each may be used.

At 102, structural imaging information is acquired, with the structural imaging information including anatomical volumetric data. For example, structural imaging information of a patient (or portion thereof) may be acquired using a structural imaging acquisition unit (e.g., structural imaging acquisition unit 510). The structural imaging acquisition unit, for example, may be configured to acquire one or more of CT, MRI, or US imaging information. Then, a structural image may be reconstructed using the structural imaging data acquired, with the structural image including the anatomical volumetric data. It may be noted that the anatomical volumetric data may refer in various embodiments to the entirety of the structural image, or just to a portion of the structural image. For example, the anatomical volumetric data may correspond to a volume of interest within the structural image.

At 104, functional imaging information is acquired, with the functional imaging information including functional volumetric data. For example, functional imaging information of a patient (or portion thereof) may be acquired using an imaging acquisition unit (e.g., functional imaging acquisition unit 530). The functional imaging acquisition unit, for example, may be configured to acquire one or more of PET or SPECT imaging information. Then, a functional image may be reconstructed using the functional imaging data acquired, with the functional image including the functional volumetric data. It may be noted that the functional volumetric data may refer in various embodiments to the entirety of the functional image, or just to a portion of the functional image. For example, the functional volumetric data may correspond to a volume of interest within the functional image. In various embodiments, the structural image (and/or the anatomical volumetric data) and the functional image (and/or the functional volumetric data) may be co-registered with each other. In some embodiments, one or more of the functional volumetric data or the structural volumetric data may be resampled.

At 106, a tissue-specific anatomical probability map is generated using the structural imaging information. It may be noted that in various embodiments more than one tissue-specific anatomical probability map may be generated. The tissue-specific anatomical probability map corresponds to the probability that a determined anatomical object correlates to potential functional data. The tissue-specific anatomical probability map may be based on a predefined model regarding the probability that a determined anatomical object or portion thereof may express functional data signals. In this model, it is assumed that the radiotracer primarily binds or accumulates in specific known types of tissues or organs. In one example scenario using a radiotracer that tends to concentrate in bones, voxels of the anatomical volumetric data corresponding to bone locations may be assigned higher probability values than voxels that correspond to soft tissue locations. As another example, higher weights may be assigned to dense soft tissues than to air regions in the lungs. For additional discussion regarding the use of intensities for functional data re-distribution, and various techniques for functional data re-distribution that may be used in connection with various embodiments, see U.S. Pat. No. 9,905,044, entitled "Systems and Methods for Functional Imaging," the subject matter of which is hereby incorporated in its entirety.

In various embodiments, the tissue-specific anatomical probability map corresponds to the probability that the intensities of specific tissue anatomical structures in the structural volumetric data correlates to the intensity distribution of potential functional data. For example, in the illustrated embodiment, at 108, the tissue-specific anatomical probability map is determined using image intensities of the structural imaging information (e.g., the anatomical volumetric data). For example, structures in a CT imaging volume may be differentiated among based on Hounsfield units.

At 110, a tissue-non-specific anatomical probability map is generated using the structural imaging information. It may be noted that in various embodiments more than one tissue-non-specific anatomical probability map may be generated. The tissue-non-specific anatomical probability map may be based on a predefined model regarding the probability that a portion of volumetric imaging data may express functional data signals. In this model, it is assumed that the radiotracer may accumulate in many types of tissues, but that, in any specific region, it is more probable that the accumulation will be related to anatomical structure borders. For example, in a region of joints or vertebrae, tracer activity may be concentrated in bones, but in another physiological situation it may be concentrated just between the bones.

In various embodiments, the tissue-non-specific anatomical probability map corresponds to the probability that the gradients of specific tissue anatomical structures in the structural volumetric data correlate to the gradient distribution of potential functional data. For example, in the illustrated embodiment, at 112, the tissue-non-specific anatomical probability map is determined using image gradients of the structural imaging information (e.g., the anatomical volumetric data). (For additional discussion regarding use of image gradients for functional data re-distribution, and various techniques for functional data re-distribution that may be used in connection with various embodiments, see U.S. Pat. No. 8,989,464, the subject matter of which is hereby incorporated in its entirety).

An example of calculating a tissue-non-specific anatomical probability map for bones in a PET-CT application, and calculating local weights for a functional data re-distribution process, is discussed in connection with FIGS. 2a-2d. In this example, the activity is concentrated or sharpened with the help of anatomical probability map gradients, but not necessarily to a specific type of tissue.

In the example, for a source voxel and a target voxel, after generation of a tissue-non-specific anatomical probability map, a direction of activity difference is determined (step 114 of FIG. 1). Next, a difference on the tissue-non-specific anatomical probability map between the source voxel and the target voxel is determined (step 116 of FIG. 1). Then, if the activity of the target voxel is greater (or equal) to the activity of the source voxel, the probability map difference is assigned a positive sign (step 118 of FIG. 1). If the activity of the target voxel is less than the activity of the source voxel, the probability map is assigned a negative sign (step 120 of FIG. 1).

Then, to determine the anatomical weight of the target voxel for a re-distribution of activity into the target voxel from the source voxel, the signed probability value for Was (from (−) to (+)) is mapped to a range between the minimum probability and the maximum probability of the map $W_a$. The process may be repeated for all voxels of the volume or a desired number of voxels (e.g., for a portion of the volume). In the examples of FIGS. 2a-2d, four cases are shown that linearly map a range [−0.9 0.9] to [0.1 1.0]. For the re-distributions of FIGS. 2a and 2b, the activity tends to concentrate between the vertebrae, while in the re-distributions of FIGS. 2c and 2d the activity tends to concentrate in the vertebrae.

With continued reference to FIG. 1, at 122, local combined anatomical probability weights are generated. The local combined anatomical probability weights in the illustrated example are generated using the tissue-specific anatomical probability map, the tissue-non-specific anatomical probability map, and the functional image data. In various embodiments, the combined anatomical probability maps (or local combined anatomical probability weights) are generated to express both the tissue-specific and tissue-non-specific probabilities based on their relative local significance. For example, in a local region, the map with more local variations will more greatly affect the functional image enhancement, based on the model being used. As different assumptions are used in each model/map, the model/maps may be combined to benefit from each, for example, by preferentially weighting for different localities where the different assumptions may provide different results, to benefit from each model of set of assumptions where appropriate, to achieve improved results.

In various embodiments, both the tissue-specific and tissue-non-specific anatomical probability maps are used to generate respective corresponding probability weights which are then combined. For example, at 124 of the illustrated example, a multiplication is performed using a tissue-specific probability weight and a tissue-non-specific probability weight to determine the local combined anatomical probability weights.

At 126, the functional image data is re-distributed using to the local combined anatomical probability weights to provide re-distributed functional volumetric data. The functional image data in the illustrated example is re-distributed between a source voxel and a plurality of neighbor voxels, with the re-distribution performed for all voxels, or alternatively all voxels of interest, for an imaging volume. Generally, in various embodiments, if it is determined that the functional volumetric data corresponds to an anatomical structure using the anatomical probability map, the functional volumetric data is redistributed to align or correspond with the anatomical structure.

It may be noted that other or additional terms may be used in the re-distribution in addition to the tissue-specific and tissue-non-specific probability weights. For example, in some embodiments, the following equation may be used:

$$\text{redistributedActivity} = \text{sourceActivity} \times W_{proximity} \times W_{activity} \times W_{anatomical\_combined} \quad \text{Equation 1:}$$

where: $W_{anatomical\_combined} = (W_{anatomical\_specific} + b_s) \times (W_{anatomical\_non-specific} + b_n)$ $W_{proximity}$ is a weighting based on proximity of the source and target voxels, $W_{activity}$ is a weighting based on the functional imaging data, and $W_{anatomical\_combined}$ is the combined weighting for the tissue-specific and tissue non-specific anatomical probability weights. Proximity weights for each of the neighboring voxel for a particular voxel to be analyzed may be determined based on a function of spatial distance and the position in the analyzed image volume, for example.

In various embodiments, the above equation is used, with the quantity of re-distributed activity between a source voxel and a neighbor target voxel is determined by the source activity multiplied by a calculated total weight (after normalization on a set of neighbor voxels). The combined anatomical weight, for each pair of voxels, may be calculated as shown in Equation 1. The constants $b_s$ and $b_n$ are parameters that help control the balance between the specific and non-specific model effects. The form in which the tissue-specific and tissue-non-specific weights are multiplied in various embodiments helps the model with the more significant local variations to be more dominant in the re-distribution. The constants $b_s$ and $b_n$ are selected, for example, based on a priori knowledge of the tracer(s) being used, for example the interaction of the tracer(s) with targeted and other tissues. It may be noted that, in some embodiments, the constants $b_s$ and $b_n$ are locally dependent on regions in the body or specific identified organs. It may further be noted that, in various embodiments, more than two different probability maps may be combined.

Examples of combinations of tissue-specific and tissue-non-specific probability weights are discussed in connection with FIGS. 3a-3g and FIGS. 4a-4g. These examples relate to a situation in which a lung lesion has radiotracer uptake, and the location of the lesion is close to the lung wall and close to a rib bone. In the example of FIGS. 3a-3g, the highest activity (e.g., functional image value) is on the lesion regions. In the example of FIGS. 4a-4g, the highest activity is directed more toward the rib bone region. For ease and simplicity of explanation, only two voxels will be considered in connection with each example, and re-distribution weights calculated only for those two voxels. In practice, however, each source voxel may be surrounded by a group of voxel neighbors, or target voxels for the re-distribution. The weight normalization may be performed on all of the neighbor group. The discussions in the examples will compare the re-distribution weights of the two voxels where P1 is the source voxel and P2 is the target voxel in connection with FIGS. 3a-3g, and where P2 is the source voxel and P1 is the target voxel in connection FIGS. 4a-4g.

Figure 3A:
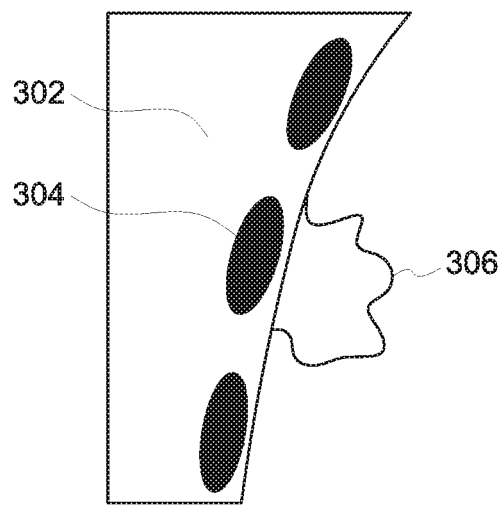
FIG. 3a depicts anatomical data in accordance with various embodiments.
Figure 3B:
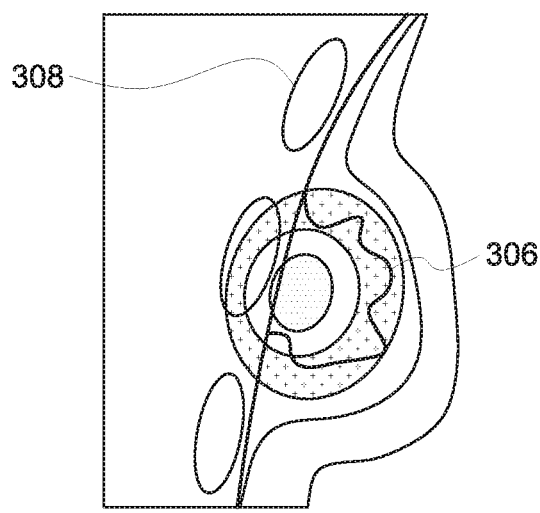
FIG. 3b depicts functional data in accordance with various embodiments.
Figure 3C:
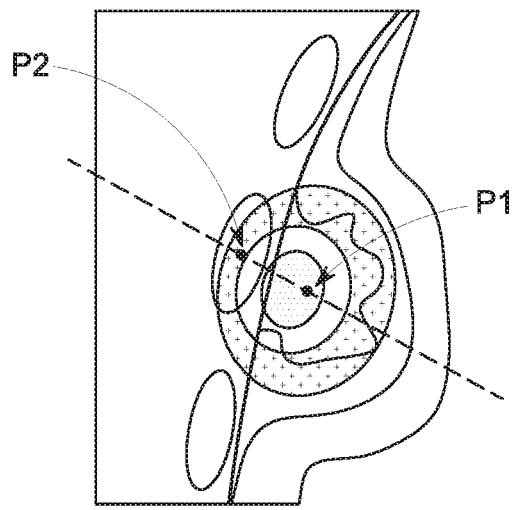
FIG. 3c depicts the two voxel positions P1 and P2 along a line for the data of FIGS. 3a and 3b.
Figure 3D:
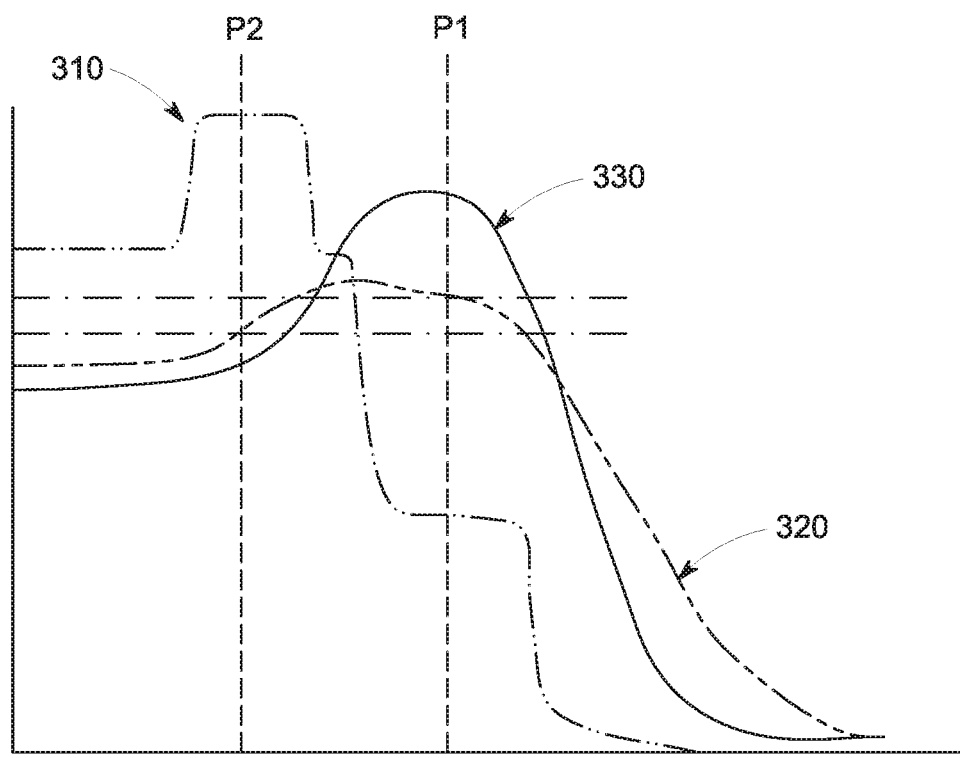
FIG. 3d depicts profiles of anatomical data, functional data, and potential enhanced functional data for the data of FIGS. 3a and 3b.
Figure 3E:
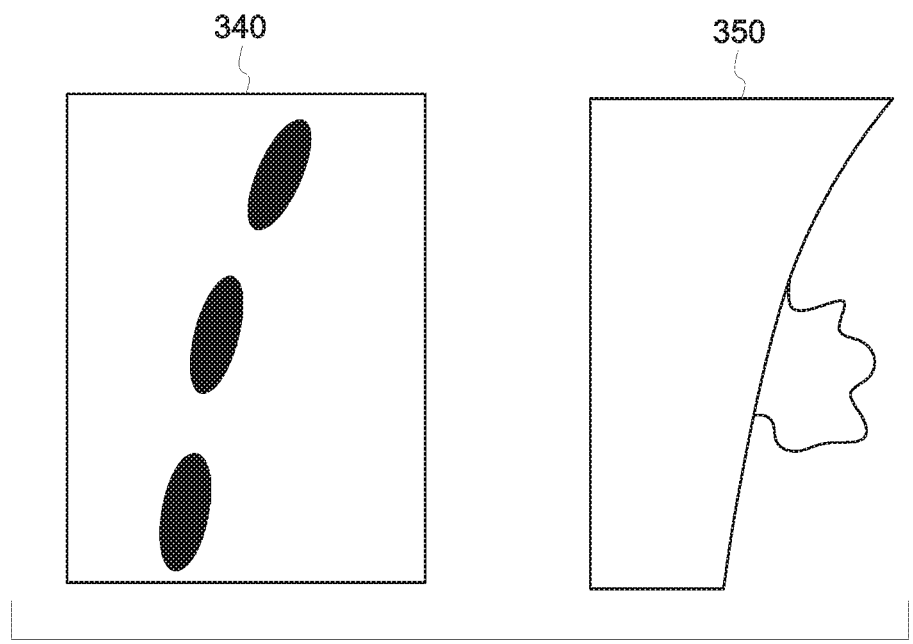
FIG. 3e depicts a tissue-non-specific probability map, and a tissue-specific probability map for the data of FIGS. 3a and 3b.
Figure 3F:
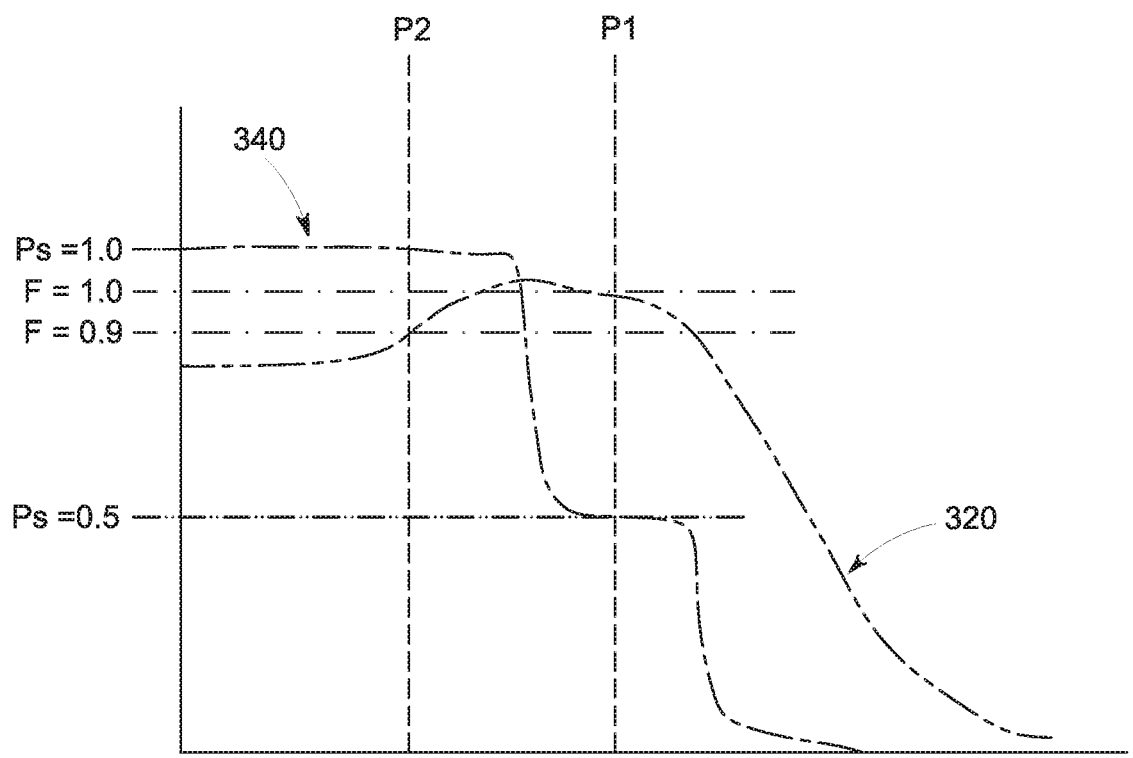
FIG. 3f depicts a comparison of the tissue-specific probability map with the original functional data for the data of FIGS. 3a and 3b.
Figure 3G:
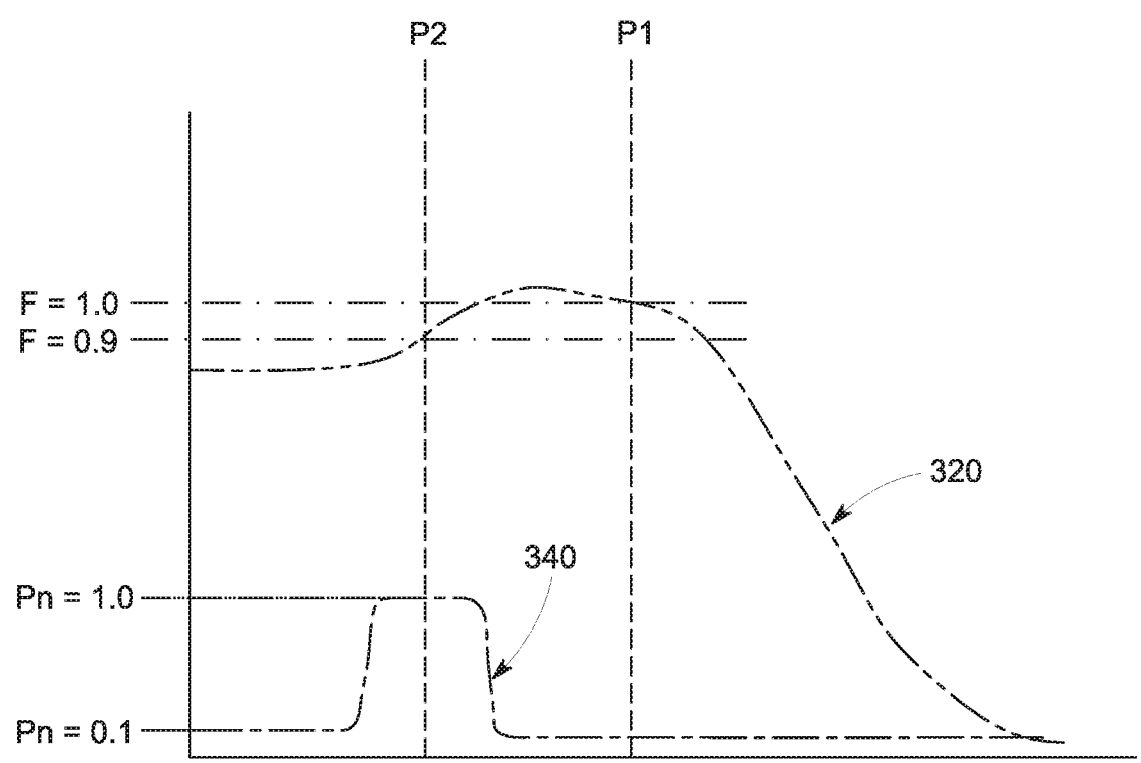
FIG. 3g depicts a comparison of the tissue-non-specific probability map compared to the original functional data for the data of FIGS. 3a and 3b.

For the first example, FIG. 3a depicts the anatomical data, including dense soft tissue 302, bone 304, and low-density soft tissue 306. FIG. 3b depicts the functional data with anatomical structure contours 308. FIG. 3c depicts the two voxel positions P1 and P2 along a line. FIG. 3d shows profiles of the anatomical data 310, the original functional data 320, and potential enhanced functional data 330. FIG. 3e depicts a tissue-non-specific probability map 340, and a tissue-specific probability map 350. FIG. 3f depicts a comparison of the tissue-specific probability map 350 compared to the original functional data 320, and FIG. 3g depicts a comparison of the tissue-non-specific probability map 340 compared to the original functional data 320. For the illustrated example, the tissue-non-specific model assigns the map value 1.0 to bone structures and the map value 0.1 to all other tissues and materials. Also, for the illustrated example, the tissue-specific model assigns the lowest value 0.0 to air and assigns increasing values with increasing densities of soft tissues, up to a dense soft tissue where the map value is saturated at 1.0. It may be noted that other value scales may be used in other embodiments.

In the example tissue-specific model, the weight that determines the redistribution from a source voxel to a target voxel uses the probability map values of the target voxel. This is due to the assumption that denser tissue (up to a threshold of dense soft tissue) has a higher probability to express higher radiotracer activity uptake. In the example tissue-non-specific model, the weights will depend on the map gradients and the correlation with the gradients of the functional data. This is due to the assumption that the uptake depends on bone structures (if existing in the surrounding volume), but the uptake can be either within the bones or outside (near) the bones.

The redistribution weights for the two voxels may be calculated for four different optional cases: a) only the tissue-specific model is considered; b) only the tissue-non-specific model is considered; c) a combination of tissue-specific and tissue-non-specific models are used; d) a combination with a regularization bias term is used. For all options, Wx_1to2 is the weight which determines how much relative functional image value will move from P1 to P2. Wx_2to1 determines how much relative functional image value will move from P2 to P1 (x is s for specific, n for non-specific, or c for combined).

For the examples under discussion, it may be noted that the combination is done as a simple multiplication of two element vectors (e.g. Wc(1)=Ws(1)*Wn(1); Wc(2)=Ws(2)*Wn(2)). In practice, however, there may be element-wise multiplication of a box of voxels by a second box of voxels.

Results of these calculations are shown in FIG. 3h. As seen in the depicted calculation results, while applying the tissue-specific model only, more functional image values will move from P1 to P2 (0.666>0.333), than from P2 to P1. This effect will not lead to the curve 330 in FIG. 3d (at least not without considering additional neighbors). While using the combined model, more functional image values will move from P2 to P1 (0.83>0.17), than from P1 to P2. This effect can lead to the curve 330 of FIG. 1d. The combination of the non-specific model with the specific model helps in this case to more concentrate the activity in a tissue structure near the bone.

It may be noted that the combination of the models may cause an undesirably overly sharp effect. Accordingly, in some embodiments, a regularization bias is added (the +2 term in FIG. 3h, as an example). In this case, the portions of data redistribution from P2 to P1 and from P1 to P2, is between the two former options. It may be noted, for example, that if the bias term is taken as a very large number, there will be no normalized variations between the weight values of the two voxels in the non-specific model. Therefore, the behavior will be as if only the specific model was used. Similarly, a bias term can be added to the specific weights alternatively.

Figure 4A:
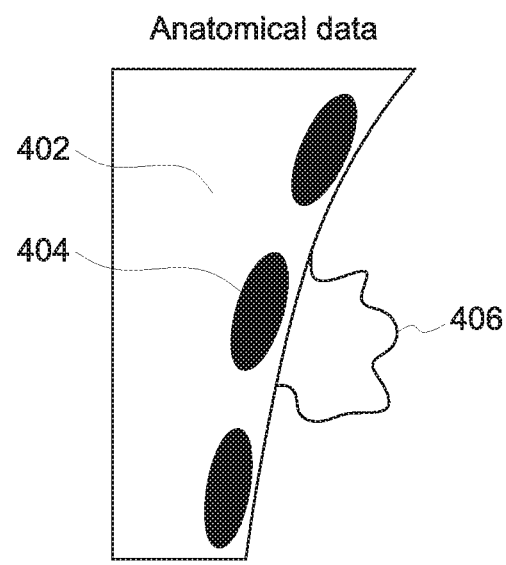
FIG. 4a depicts anatomical data in accordance with various embodiments.
Figure 4B:
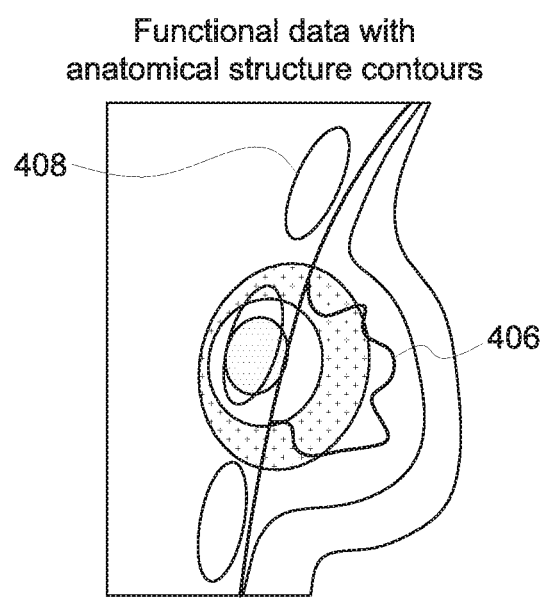
FIG. 4b depicts functional data in accordance with various embodiments.
Figure 4C:
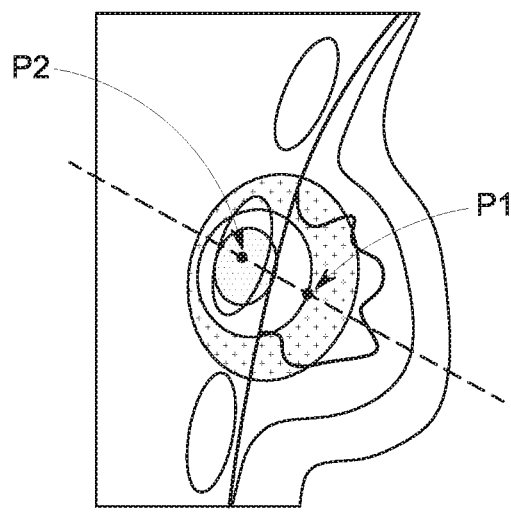
FIG. 4c depicts the two voxel positions P1 and P2 along a line for the data of FIGS. 4a and 4b.
Figure 4D:
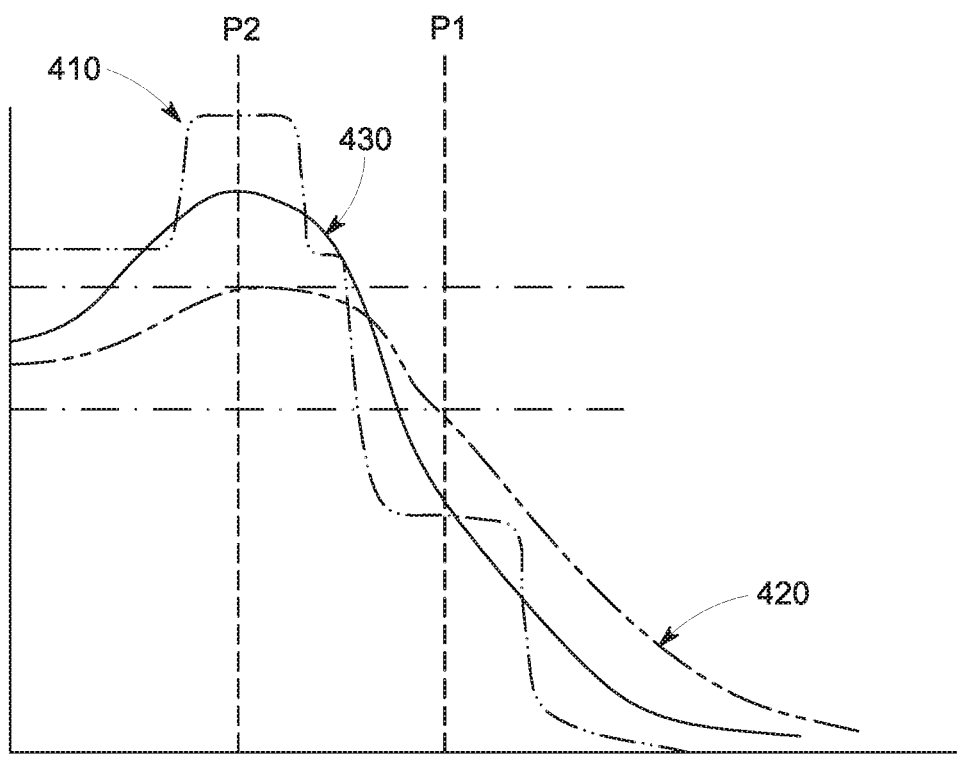
FIG. 4d depicts profiles of anatomical data, functional data, and potential enhanced functional data for the data of FIGS. 4a and 4b.
Figure 4E:
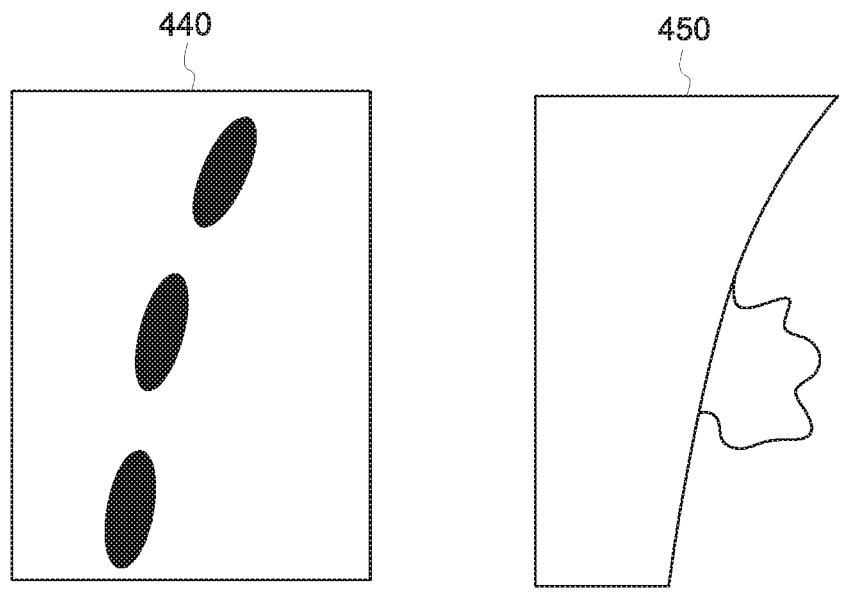
FIG. 4e depicts a tissue-non-specific probability map, and a tissue-specific probability map for the data of FIGS. 4a and 4b.
Figure 4F:
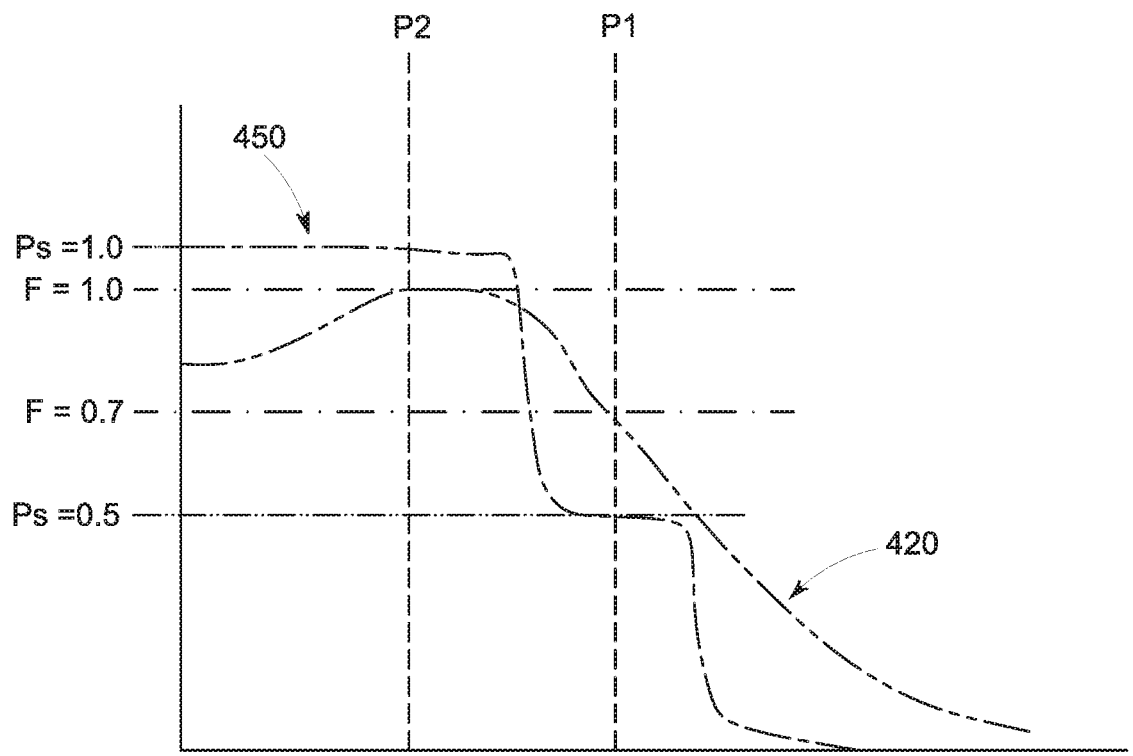
FIG. 4f depicts a comparison of the tissue-specific probability map with the original functional data for the data of FIGS. 4a and 4b.
Figure 4G:
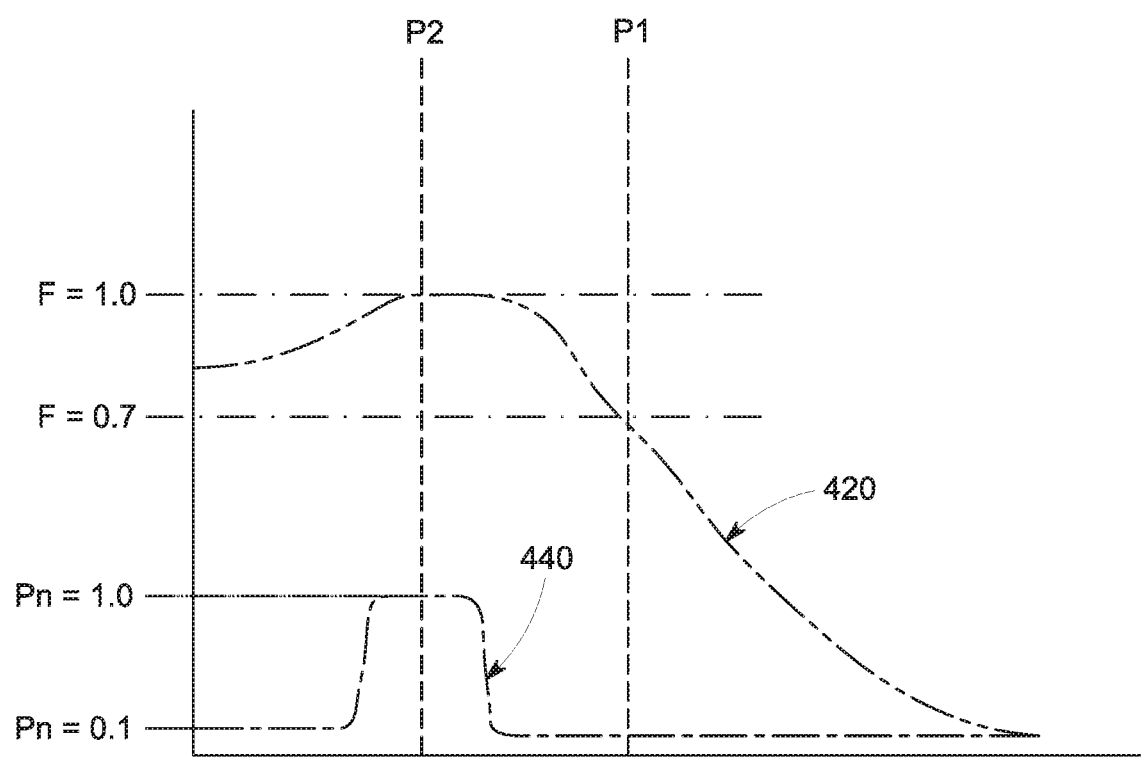
FIG. 4g depicts a comparison of the tissue-non-specific probability map compared to the original functional data for the data of FIGS. 4a and 4b.

For the second example, FIG. 4a depicts the anatomical data, including dense soft tissue 402, bone 404, and low-density soft tissue 406. FIG. 4b depicts the functional data with anatomical structure contours 408. FIG. 4c depicts the two voxel positions P1 and P2 along a line. FIG. 4d shows profiles of the anatomical data 410, the original functional data 420, and potential enhanced functional data 430. FIG. 4e depicts a tissue-non-specific probability map 440, and a tissue-specific probability map 450. FIG. 4f depicts a comparison of the tissue-specific probability map 450 compared to the original functional data 420, and FIG. 4g depicts a comparison of the tissue-non-specific probability map 440 compared to the original functional data 420.

FIGS. 4a-4h relate to a situation in which the highest activity is on P2 within a bone structure. In this case, the non-specific model will increase the activity redistribution to within the bone structure. If the specific model alone is used, more functional image values will move from P1 to P2 (0.666>0.333), than from P2 to P1, as before. However, with the combination of the non-specific model, the effect is much greater (0.95>>0.05). The combination of the non-specific model with the specific model helps in this case to more concentrate the activity in a tissue structure within the bone.

It may be noted that, in the application of the models in the examples discussed in connection with FIGS. 3a-3h and 4a-4h, there is an a priori assumption that the activity spot is less probably distributed evenly between both the adjacent lesion and rib. Such an even distribution is possible, but there is a low probability of such an even distribution.

At 128, an image is generated using the re-distributed functional volumetric data. The image, for example, may be displayed (e.g. via a screen or printout). The image in various embodiments may display only the redistributed functional data, or may display one or more of the anatomical structures of the structural image or the original, non-redistributed functional data. As one example, the redistributed functional data may be overlaid with the anatomical data on one portion of a screen, while the original, non-redistributed functional data is displayed on a different portion of a screen, allowing a user to compare redistributed and non-redistributed images.

Figure 5:
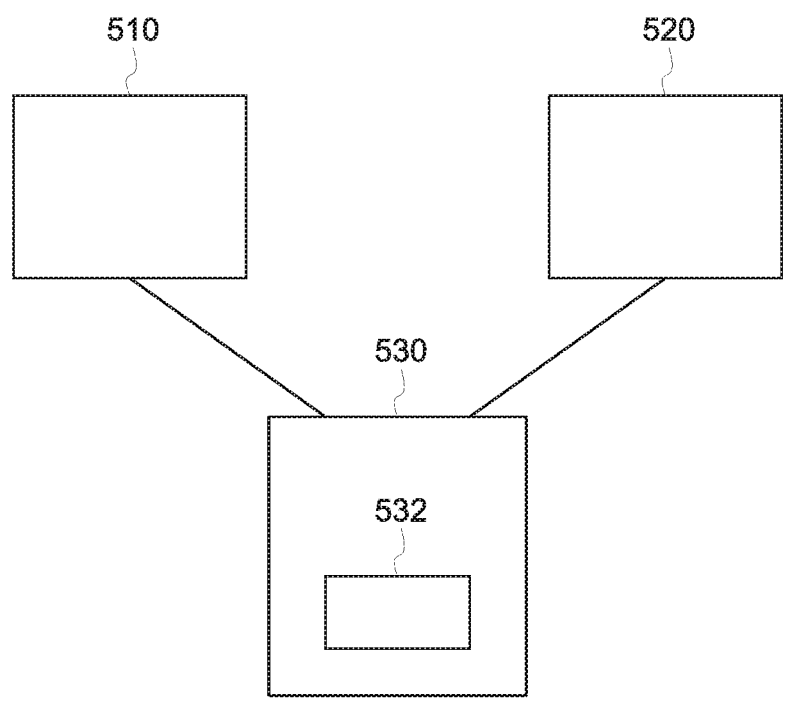
FIG. 5 is a schematic block diagram illustrating a system in accordance with various embodiments described herein.

FIG. 5 illustrates a system 500 formed in accordance with various embodiments. As seen in FIG. 1, the system 500 includes a structural imaging acquisition unit 510, a functional imaging acquisition unit 520, and a processing unit 530. Generally, the structural imaging acquisition unit 510 is configured to perform a scan to acquire structural or anatomical imaging information, and the functional imaging acquisition unit 520 is configured to perform a scan to acquire functional imaging information. The structural imaging acquisition unit 510, for example, may be configured to perform one or more of X-ray, CT, MRI, or US scans. The functional imaging acquisition unit 520, for example, may be configured to perform one or more of PET or SPECT scans. It may be noted that the structural imaging acquisition unit 510 and the functional imaging acquisition unit 520 may be part of a single installation, or multi-modality imaging system.

The processing unit 530 may be located remotely from the imaging acquisition units, or in the same location. Generally, the processing unit 530 is configured to obtain a structural image including anatomical volumetric data. For example, the structural image may be obtained by reconstructing an image using the structural imaging information acquired by the structural imaging acquisition unit 510 (or obtaining such an image that has already been reconstructed. Also, the processing unit 530 is configured to obtain a functional image including functional volumetric data. For example, the functional image may be obtained by reconstructing an image using the functional imaging information acquired by the functional imaging acquisition unit 520 (or obtaining such an image that has already been reconstructed). The depicted processing unit 530 is also configured to determine an anatomical probability map corresponding to a probability that a determined anatomical object correlates to potential functional data, and to redistribute the functional volumetric data using the anatomical probability map to provide redistributed functional volumetric data. For example, the depicted processing unit 530 in various embodiments is configured to perform one or more aspects of method 100 discussed herein. Further, the processing unit 530 may include or be coupled to a display that may be used to display an image generated by the processing unit 530 using the re-distributed volumetric data.

The depicted processing unit 530 includes a memory 532. The processing unit 530 is depicted as including a single processing unit 530; however, the block for the processing unit 530 may be understood as representing one or more processors that may, in some embodiments, be distributed or remote from each other.

The processing unit 530 may include processing circuitry configured to perform one or more tasks, functions, or steps discussed herein. It may be noted that "processing unit" as used herein is not intended to necessarily be limited to a single processor or computer. For example, the processing unit 530 may include multiple processors and/or computers, which may be integrated in a common housing or unit, or which may distributed among various units or housings.

Generally, various aspects (e.g., programmed modules) of the processing unit 530 act individually or cooperatively with other aspects to perform one or more aspects of the methods, steps, or processes discussed herein (e.g., method 100, or aspects thereof). In the depicted embodiment, the memory 532 includes a tangible, non-transitory computer readable medium having stored thereon instructions for performing one or more aspects of the methods, steps, or processes discussed herein. It may be noted other aspects of the system 500 (e.g., the acquisition units) may include similar processing units (e.g., including at least one processor and associated memory configured to act individually or cooperatively with other aspects to perform one or more aspects of the methods, steps, or processes discussed herein).

It may be noted that systems and methods described herein may provide improved imaging benefits in many clinical applications. For example, PET-CT $^{18}$F-FDG may be used for various types of cancer imaging. In this application, the tissue-specific model may be based on soft-tissue density with saturation for higher densities as in bones, and the tissue-non-specific model can be based on hard and soft bone gradient structures.

As another example, PET-CT $^{68}$Ga-PSMA may be used to assess prostate cancer lesion metastasizes in the bones, for example during treatment follow-up. In this application, the tissue-specific model can be based on hard and soft bone CT image intensities. The tissue-non-specific model may be based on CT soft-tissue image gradients, since the tracer also accumulates normally in several body organs.

As another example, PET-CT $^{68}$Ga-DOTATATE may be used to assess neuroendocrine tumors and lesions. In this application, the tissue-specific model may be based on both soft-tissue and bone image densities, and the tissue-non-specific model may be based on CT image gradients of soft-segmented internal organs such as kidneys, liver and spleen.

As another example, for a brain PET-CT or PET-MM application, the tissue-specific model may be based on image intensities of gray and white matter structures, that may be visible on MRI or CT, depending on the imaging system operation protocol. The tissue-non-specific model may be based on image gradients of sporadic/irregular tissue structures that are different than gray and white matters (e.g. potential tumors or hemorrhages).

As one more example, SPECT-CT $^{177}$Lu-PSMA may be used to assess prostate cancer lesion metastasizes in the bones and distribution in healthy organs, for example during treatment courses using the same tracer. In this application, the tissue-specific model may be based on image intensities of hard and soft bone. The tissue-non-specific model may be based on CT image gradients of soft-segmented internal organs such as kidneys, liver and spleen, or, alternatively, just on soft-tissue densities.

Figure 6:
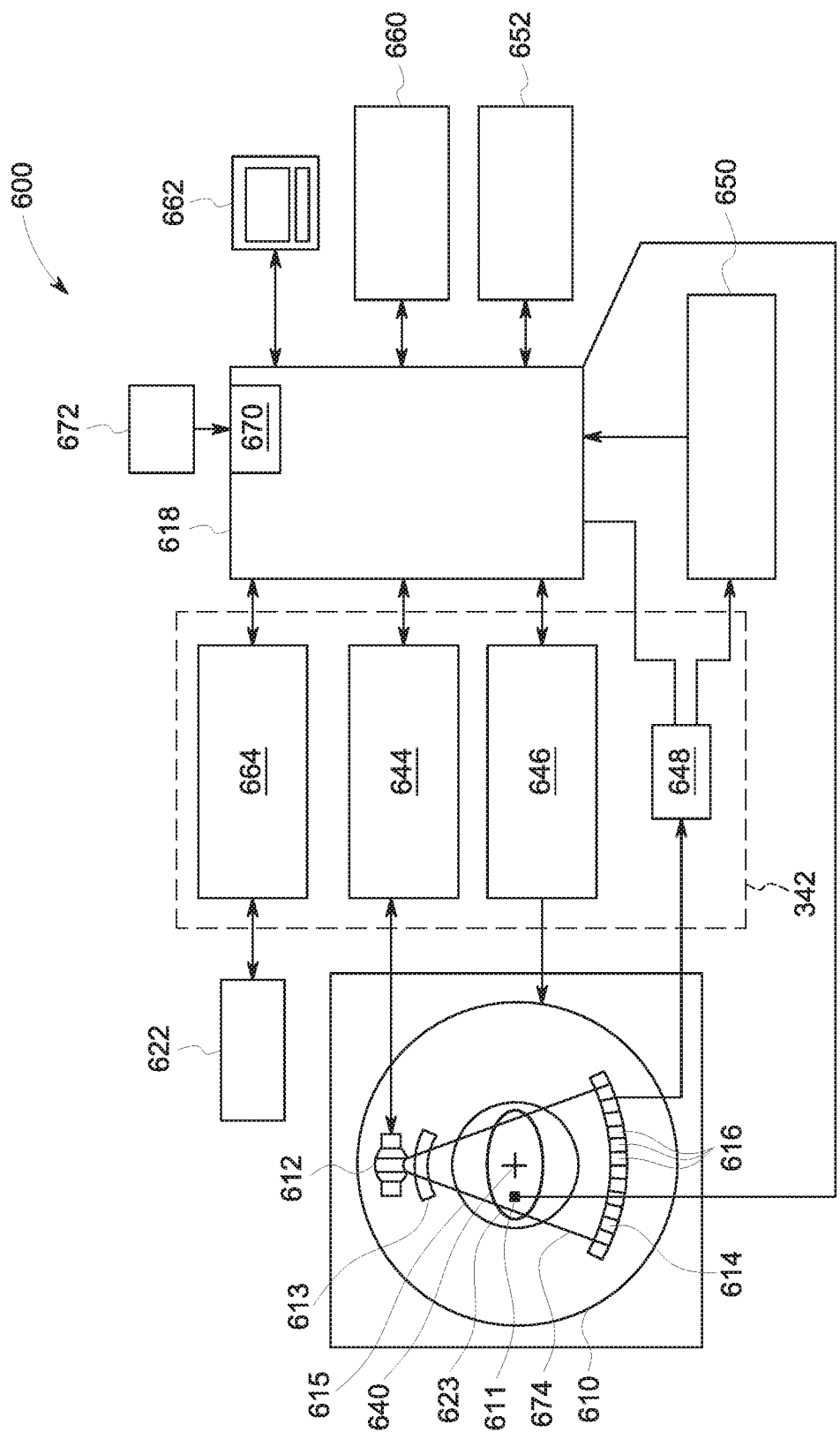
FIG. 6 is a schematic block diagram illustrating an imaging system in accordance with various embodiments described herein.

FIG. 6 illustrates a schematic diagram of an exemplary CT imaging system 600 that may be utilized to implement various embodiments discussed herein (e.g., as all or a portion of the structural imaging acquisition unit 510). Although the CT imaging system 600 is illustrated as a standalone imaging system, it should be noted that the CT imaging system 600 may form part of a multi-modality imaging system in some embodiments. For example, the multi-modality imaging system may include the CT imaging system 600 and a positron emission tomography (PET) imaging system, or a single photon emission computed tomography (SPECT) imaging system. It should also be noted that in various embodiments one or more imaging modalities other than CT may be employed. It should also be understood that other imaging systems capable of performing the functions described herein are contemplated as being used.

The CT imaging system 600 includes a gantry 610 that has the X-ray source 612 that projects a beam of X-rays toward the detector array 614 on the opposite side of the gantry 610. A source collimator 613 and a bowtie filter module (not shown) are provided proximate the X-ray source 612. The detector array 614 includes a plurality of detector elements 616 that are arranged in rows and channels that together sense the projected X-rays that pass through a patient 623 (e.g., object of interest). The imaging system 600 may include a physiologic sensor 611 (e.g., electrocardiogram (ECG), a respiratory sensor) proximate to the patient 623 for cardiac or respiratory gating.

A motorized table 622 is utilized to move the patient 623 into and out of the gantry 610 at a table feed rate. Particularly, the table 622 moves at least a portion of the patient 623 through a gantry opening 615 along a z-axis that extends through the gantry 610. Further, the table 622 may be used to move the patient 623 vertically within the bore of the gantry 610.

The depicted detector array 614 includes a plurality of detector elements 616. Each detector element 616 produces an electrical signal, or output, that represents the intensity of an impinging X-ray beam and hence allows estimation of the attenuation of the beam as it passes through the patient 623. During a scan to acquire the X-ray projection data, the gantry 610 and the components mounted thereon rotate about a center of rotation 640. FIG. 6 shows only a single row of detector elements 616 (i.e., a detector row). However, the multi-slice detector array 614 includes a plurality of parallel detector rows of detector elements 616 such that projection data corresponding to a plurality of slices can be acquired simultaneously during a scan.

In the exemplary embodiment, the X-ray source 612 and the detector array 614 are rotated with the gantry 610 within the imaging plane and around the patient 623 to be imaged such that the angle at which an X-ray beam 674 intersects the patient 623 constantly changes. A group of X-ray attenuation measurements, i.e., projection data, from the detector array 614 at one gantry angle is referred to as a "view" or "projection." A "scan" of the patient 623 comprises a set of views made at different gantry angles, or view angles, during one or more revolutions of the X-ray source 612 and the detector array 614. In a CT scan, the projection data is processed to reconstruct an image that corresponds to a three-dimensional volume taken of the patient 623. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

Rotation of the gantry 610, the operation of the X-ray source 612, and position of the motorized table 622 are governed by an acquisition subsystem 642 based on one or more scan settings (e.g., tube current/voltage, focal spot size, duty cycle, kV pair, rotation speed, collimation width, field of view size, body dose, exposure time, head dose, helical pitch) defined by a scan prescription or protocol. The acquisition subsystem 642 includes an X-ray controller 644 that provides power and timing signals to the X-ray source 612 based on the scan settings defined by the scan prescription or protocol. The X-ray controller 644 may deliver power (e.g., tube current, tube voltage) and/or configure the X-ray source 612 to project X-rays having a certain field of view and/or collimation width (e.g., collimation slab) based on the scan settings defined by the scan prescription or protocol. Additionally or alternatively, the X-ray controller 644 may control a focal spot size of the X-ray source 612 based on the scan settings defined by the scan prescription or protocol. Optionally, for dual-energy CT scans, the X-ray controller 644 may define the dual energy levels (e.g., kV pair) and duty cycle of the X-rays emitted by the X-ray source 612.

The acquisition subsystem 642 also includes a gantry motor controller 646 that controls the rotational speed and position of the gantry 610. For example, the gantry motor controller 346 may rotate the gantry 610 at a rotational velocity based on the scan settings defined by the scan prescription or protocol.

In addition, the acquisition subsystem 642 may also include a table motor controller 664 that controls the motorized table 622 to position the patient 623 in the gantry 610 based on the scan settings defined by the scan prescription or protocol. Particularly, the motorized table 622 moves at least a portion of the patient 623 through the gantry opening at a table feed rate.

The scan prescription or protocol may be stored on a storage device 652 which is communicatively coupled to the acquisition subsystem 642. The storage device 652 may be a tangible and non-transitory computer readable medium such as flash memory, RAM, ROM, EEPROM, and/or the like. The scan prescription or protocol may be defined by a processing unit 318.

The processing unit 618 may include one or more processors. Optionally, the processing unit 618 may include a central controller circuit (CPU), one or more microprocessors, a graphics controller circuit (GPU), or any other electronic component capable of processing inputted data according to specific logical instructions. Additionally or alternatively, the processing unit 618 may execute instructions stored on a tangible and non-transitory computer readable medium (e.g., the storage device 652, integrated memory of the processing unit 618). The processing unit 618 receives the projection data from the detector array 614 and processes the projection data to reconstruct an image of the patient 623.

The processing unit 618 is operably coupled to a display 662 and the user interface 660. The display 662 may include one or more liquid crystal displays (e.g., light emitting diode (LED) backlight), organic light emitting diode (OLED) displays, plasma displays, CRT displays, and/or the like. The display 662 allows the operator to observe the reconstructed image and other data generated by the processing unit 618. For example, the display 662 may display patient information, one or more CT images, components of a display interface, measurements, diagnosis, treatment information, and/or the like.

The user interface 660 controls operations of the CT imaging system 600 and is configured to receive inputs (e.g., CID) from the user. The user interface 660 may include a keyboard, a mouse, a touchpad, one or more physical buttons, and/or the like. Optionally, the display 662 may be a touch screen display, which includes at least a portion of the user interface 642. For example, the user may select one or more user selectable elements shown on the display by touching or making contact with touch sensitive portions of the display 662.

A data acquisition system (DAS) 648 in the acquisition subsystem 642 samples analog data from detector elements 616 and converts the data to digital signals, the projection data, for subsequent processing. An image reconstructor circuit 650 receives the projection data from the DAS 648 and performs an image reconstruction. The image reconstructor circuit 650 may include one or more processors, field programmable arrays, one or more ASICs, a CPU, or any other electronic component capable of processing inputted data according to specific logical instructions. Additionally or alternatively, the image reconstructor circuit 650 may execute programmed instructions stored on a tangible and non-transitory computer readable medium (e.g., the storage device 652, integrated memory of the image reconstructor circuit 650). For example, the one or more processors may perform one or more operations by executing programmed instructions stored on the storage device 652 and/or integrated memory such as EEPROM. The image reconstructor circuit 650 may generate the resultant medical image based on reconstructed settings received via the user interface 660 and/or based on the scan attributes. The reconstruction settings may include select keV energy level(s), iterative reconstruction (e.g., adaptive statistical reconstruction), direct multi-planar reconstruction, algorithmic reconstruction, and/or the like.

The projection data is processed by the image reconstructor circuit 650 to reconstruct resultant medical images that corresponds to a two dimensional (2D) slice taken through the patient 623. In some embodiments, a 3D reconstruction may be reconstructed directly. The image reconstructor circuit 350 may convert the attenuation measurements associated with the projection data into a medical image of the patient 623. The attenuation measurements are typically converted into units of "CT numbers" or Hounsfield units (HU). The image is represented as a matrix of numbers, with each individual number in the image matrix representing a three-dimensional (3D) volume element in the scanned part, called a "voxel." To obtain a visual image, each voxel is represented as a 2D picture element, or "pixel." Each pixel has a shade of gray based on the HU value representing the attenuation measurement within the corresponding voxel. For example, the HU value may correspond to a brightness of each pixel such that a pixel having a higher HU value may be brighter relative to a pixel having a lower HU value. The reconstructed medical images generated by the image reconstructor circuit 650 are input to the processing unit 618 that stores the image in the storage device 652. Optionally, the image reconstructor circuit 650 may be integrated with and/or similar operations may be performed by the processing unit 618.

Additionally or alternatively, the processing unit 618 includes a device 670, for example, a CD-ROM drive, DVD drive, magnetic optical disk (MOD) device, and/or any other digital device including a network connecting device such as an Ethernet device for reading instructions and/or data from a tangible non-transitory computer-readable medium 672.

Figure 7:
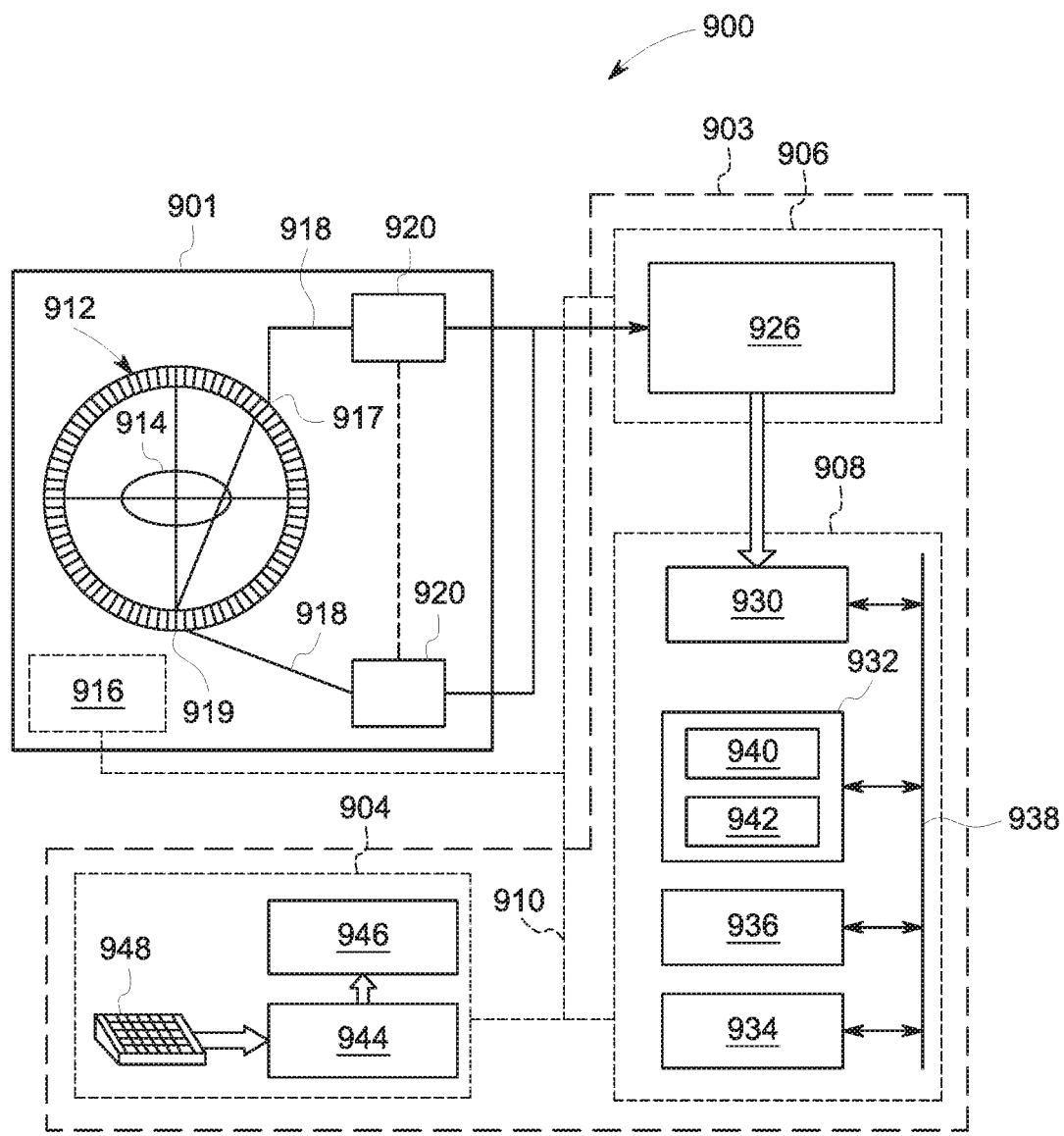
FIG. 7 is a schematic block diagram illustrating an imaging system in accordance with various embodiments described herein.

FIG. 7 is a block diagram of an exemplary embodiment of a PET system 900 in which various embodiments may be implemented. The PET system 900, for example, may form all or a portion of the functional imaging acquisition unit 520. The PET system 900 includes a PET scanner 901 and a controller 903 to control image reconstruction processes. The controller 903 includes an operator workstation 904 and a processor 905. The processor 905 includes a data acquisition processor 906 and an image reconstruction processor 908. The PET scanner 901, operator workstation 904, data acquisition processor 906 and image reconstruction processor 908 are interconnected via a communication link 910 (e.g., a serial communication or wireless link). The PET scanner 901, which typically includes a gantry (not shown in FIG. 7), acquires scan data and transmits the data to the data acquisition processor 906. The operation of the PET scanner 901 is controlled from operator workstation 904. The data acquired by data acquisition processor 906 is reconstructed using image reconstruction processor 908.

The PET scanner 901 may operate, using, for example, a plurality of detector rings. One such detector ring, detector ring 912, is illustrated in FIG. 7, which includes detector elements formed in accordance with various embodiments. In various embodiments, the detector elements may include one or more of scintillators, tube photo-multipliers or Silicon photo-multipliers. The detector ring 912 includes a central opening, in which an object 914 (e.g., a patient) may be positioned, using, for example, a motorized table that is aligned with the central axis of the ring 912. The motorized table moves the object 914 into the central opening of the ring 912, in response to one or more commands received from operator workstation 904. A PET scanner controller 916, also referred to as a gantry controller, is provided (e.g., mounted) in the PET scanner 901. The PET scanner controller 916 responds to the commands received from the operator workstation 904 through the communication link 910. Therefore, the operation of the PET scanner 901 is controlled from the operator workstation 904 through the PET scanner controller 916.

The detector ring 912 includes a plurality of detector elements for performing a PET scan of the object 914. For example, there may be 420 crystals per ring and 24 rings in the scanner. As shown in FIG. 10, the detector ring 912 includes a first detector element 917, a second detector element 919, and several other detectors. It should be noted that the detector elements are referred to as the first detector element and the second detector element, only to differentiate location in FIG. 7. The first detector element 917, like the other detectors, includes a set of scintillator crystals arranged in a matrix that is disposed in front of a plurality of photosensors. When an annihilation photon impinges on a crystal on a detector, the annihilation photon produces a scintillation in the crystal. Each photosensor produces an analog or digital signal on the communication line 918 when a scintillation event occurs. A set of acquisition circuits 920 is provided within the PET scanner 901 to receive these analog or digital signals. The acquisition circuits 920 may include analog-to-digital converters to digitize analog signals, processing electronics to quantify event signals and a time measurement unit to determine time of events relative to other events in the system. For example, this information indicates when the event took place and the identity of the scintillation crystal that detected the event. The acquisition circuits produce digital data indicating the location, time and total energy of the event. This event data is transmitted through a communication link, for example, a cable, to a coincidence detector or processor 926.

The coincidence detector 926 receives the event data packets from the acquisition circuits 920 and determines if any two of the detected events are in coincidence. In this context, the coincidence is determined by a number of factors. First, the time markers in each event data packet must be within a predetermined time period, for example, 6 ns, of each other. Secondly, the LOR formed by a straight line joining the two detectors that detect the coincidence event should pass through the field of view in PET scanner 901. Events that cannot be paired are discarded. Coincident event pairs are recorded as a coincidence data packet that is communicated through a communication link to a sorter 930 in the image reconstruction processor 908.

The image reconstruction processor 908 includes the sorter 930, a memory module 932, an image CPU 934, an array processor 936, and a back-plane bus 938. The sorter 930 counts all events that occur along each projection ray and organizes them into a coincidence data set. In one embodiment, this data set is organized as a data array 940, referred to as a sinogram. The data array 940 is stored in the memory module 932. The back-plane bus 938 is linked to the communication link 910 through the image CPU 934, which controls communication through the back-plane bus 938. The array processor 936 is also connected to the back-plane bus 938, receives the data array 940 as an input, and reconstructs images in the form of the image arrays 942. The resulting image arrays 942 are stored in the memory module 932.

The images stored in the image array 942 are communicated by the image CPU 934 to the operator workstation 904. The operator workstation 904 includes a CPU 944, a display device 946, and an input device 948. The CPU 944 connects to the communication link 910 and receives inputs (e.g., user commands) from the input device 948, which may be, for example, a keyboard, mouse, or a touch-screen panel. The operator can control the calibration of the PET scanner 901, the configuration of the PET scanner 901, and the positioning of the object 914 for a scan through the input device 948 and associated control panel switches. Similarly, the operator can also control the display of the resulting image on the display device 946 and perform image-enhancement functions, using programs executed by the workstation CPU 944.

The processor 905 is configured to process the scan data received from the detector elements. The scan data includes, for example, sinogram and timing information that is received by processor 905 from the detector elements during an imaging scan. The timing information in one embodiment is the difference in time at which two annihilation photons emitted in an annihilation event are detected by detector elements. The timing information may include time stamp information relating to a measured annihilation event detected by a pair of detector elements, for example, the first detector element 917 and the second detector element 919, for the PET system 900. The time stamp information is the time at which each annihilation photon is detected by a detector element, which in various embodiments.

The timing information is received by detectors, which include, for example, a block of 36 scintillator crystals attached to an array of photosensors. The scintillator crystals convert the incoming annihilation photon from the patient into a plurality (e.g., several thousand) of light photons (e.g., visible or near UV), which are detected by the photosensors. The proportion of light photons detected by each photosensor channel is used to determine which of the 36 crystals received the incoming photon. The timing signal is determined by processing the leading edge of the signals, to estimate the arrival of the light photons at the light sensors 34 of, for example, the SIPM. This timing signal is then digitized and processed subsequently.

The energy and timing information are used to reconstruct an image of the object 914, scanned by the PET system 900. The reconstruction may include, for example, a two-dimensional or three-dimensional reconstruction. The timing data of each detector element may be configured as a timing bias matrix with a timing recovery value for each set of projection rays of the PET system 900. It should be noted that a detector element pair detects the projection rays from an annihilation event. The timing bias data of each detector element pair corresponding to the projection ray is stored in the memory module 932 of the PET system 900.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "processing unit," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A system comprising:
  a structural imaging acquisition unit configured to perform a structural scan to acquire structural imaging information of a patient;
  a functional imaging acquisition unit configured to perform a functional scan to acquire functional imaging information of a patient;
  one or more processors configured to:
    generate a tissue-specific anatomical probability map using the structural imaging information;
    generate a tissue-non-specific anatomical probability map using the structural imaging information;
    generate local combined anatomical probability weights using the tissue-specific anatomical probability map, the tissue-non-specific anatomical probability map, and the functional image data;
    re-distribute the functional image data using the local combined anatomical probability weights to provide re-distributed functional volumetric data; and
    generate an image using the re-distributed functional volumetric data.

2. The system of claim 1, wherein the one or more processors are configured to determine the tissue-specific anatomical probability map using image intensities of the structural imaging information.

3. The system of claim 1, wherein the one or more processors are configured to determine the tissue-non-specific anatomical probability map using image gradients of the structural imaging information.

4. The system of claim 1, wherein the one or more processors are configured to:
  determine, for a source voxel and a target voxel, a direction of an activity difference;
  determine a difference on the tissue-non-specific anatomical probability map between the source voxel and the target voxel;
  if the activity of target voxel is greater than or equal to the activity of the source voxel, assign a positive sign to the difference; and
  if the activity of the target voxel is less than the activity of the source voxel, assign a negative sign to the difference.

5. The system of claim 1, wherein the one or more processors are configured to perform a multiplication of a tissue-specific probability weight and a tissue-non-specific probability weight to determine the local combined anatomical probability weights.

6. The system of claim 5, wherein the one or more processors are configured to re-distribute the functional volumetric data using the following equation:

$$\text{redistributedActivity} = \text{sourceActivity} \times W_{proximity} \times W_{activity} \times W_{anatomical\_combined}$$

where: $W_{anatomical\_combined}=(W_{anatomical\_specific}+b_s)\times(W_{anatomical\_non-specific}+b_n)$.

7. The system of claim 6, wherein the constants bs and bn are locally dependent.

8. The system of claim 1, wherein the one or more processors are configured to apply a regularization bias to a tissue-non-specific probability weight.

9. A method comprising:
   obtaining structural imaging information of a patient including anatomical volumetric data;
   obtaining functional imaging information of the patient including functional volumetric data;
   generating a tissue-specific anatomical probability map using the structural imaging information;
   generating a tissue-non-specific anatomical probability map using the structural imaging information;
   generating local combined anatomical probability weights using the tissue-specific anatomical probability map, the tissue-non-specific anatomical probability map, and the functional image data;
   re-distributing the functional image data using the local combined anatomical probability weights to provide re-distributed functional volumetric data; and
   generating an image using the re-distributed functional volumetric data.

10. The method of claim 9, wherein the tissue-specific anatomical probability map is determined using image intensities of the structural imaging information.

11. The method of claim 9, wherein the tissue-non-specific anatomical probability map is determined using image gradients of the structural imaging information.

12. The method of claim 9, further comprising:
   determining, for a source voxel and a target voxel, a direction of an activity difference;
   determining a difference on the tissue-non-specific anatomical probability map between the source voxel and the target voxel;
   if the activity of target voxel is greater than or equal to the activity of the source voxel, assigning a positive sign to the difference; and
   if the activity of the target voxel is less than the activity of the source voxel, assigning a negative sign to the difference.

13. The method of claim 9, further comprising performing a multiplication of a tissue-specific probability weight and a tissue-non-specific probability weight to determine the local combined anatomical probability weights.

14. The method of claim 13, wherein the functional volumetric data is re-distributed using the following equation:

$$redistributedActivity = sourceActivity \times W_{proximity} \times W_{activity} \times W_{anatomical\_combined}$$

where: $W_{anatomical\_combined}=(W_{anatomical\_specific}+b_s)\times(W_{anatomical\_non-specific}+b_n)$.

15. The method of claim 14, wherein the constants bs and bn are locally dependent.

16. The method of claim 9, further comprising applying a regularization bias to a tissue-non-specific probability weight.

17. A tangible and non-transitory computer readable medium comprising one or more computer software modules configured to direct one or more processors to:
   obtain structural imaging information of a patient including anatomical volumetric data;
   obtain a functional imaging information of the patient including functional volumetric data;
   generate a tissue-specific anatomical probability map using the structural imaging information;
   generate a tissue-non-specific anatomical probability map using the structural imaging information;
   generate local combined anatomical probability weights using the tissue-specific anatomical probability map, the tissue-non-specific anatomical probability map, and the functional image data;
   re-distribute the functional image data using the local combined anatomical probability weights to provide re-distributed functional volumetric data; and
   generate an image using the re-distributed functional volumetric data.

18. The tangible and non-transitory computer readable medium of claim 17, wherein the one or more computer software modules are further configured to direct the one or more processors to determine the tissue-specific anatomical probability map using image intensities of the structural imaging information.

19. The tangible and non-transitory computer readable medium of claim 17, wherein the one or more computer software modules are further configured to direct the one or more processors to determine the tissue-non-specific anatomical probability map using image gradients of the structural imaging information.

20. The tangible and non-transitory computer readable medium of claim 17, wherein the one or more computer software modules are further configured to direct the one or more processors to perform a multiplication of a tissue-specific probability weight and a tissue-non-specific probability weight to determine the local combined anatomical probability weights.

* * * * *